US011311485B2

(12) United States Patent
Allen et al.

(10) Patent No.: US 11,311,485 B2
(45) Date of Patent: Apr. 26, 2022

(54) SELF-ASSEMBLED PARTICLES FOR TARGETED DELIVERY OF IMMUNOMODULATORS TO TREAT AUTOIMMUNITY AND CANCER

(71) Applicants: UNIVERSITY OF MARYLAND, BALTIMORE COUNTY, Baltimore, MD (US); UNIVERSITY OF MARYLAND, BALTIMORE, Baltimore, MD (US); NORTHWESTERN UNIVERSITY, Evanston, IL (US)

(72) Inventors: Marilyn Allen, Robbinsville, NJ (US); Evan Scott, Winnetka, IL (US); Amit Golding, Baltimore, MD (US); Gregory Szeto, Baltimore, MD (US); Nicholas B. Karabin, Evanston, IL (US)

(73) Assignees: University of Maryland, Baltimore County, Baltimore, MD (US); University of Maryland, Baltimore, Baltimore, MD (US); Northwestern University, Evanston, IL (US)

(*) Notice: Subject to any disclaimer, the term of this patent is extended or adjusted under 35 U.S.C. 154(b) by 60 days.

(21) Appl. No.: 16/568,396

(22) Filed: Sep. 12, 2019

(65) Prior Publication Data

US 2020/0078300 A1 Mar. 12, 2020

Related U.S. Application Data

(60) Provisional application No. 62/730,157, filed on Sep. 12, 2018.

(51) Int. Cl.
| | |
|---|---|
| *A61K 31/4706* | (2006.01) |
| *A61K 31/573* | (2006.01) |
| *A61K 31/52* | (2006.01) |
| *A61P 37/06* | (2006.01) |
| *A61K 9/127* | (2006.01) |
| *A61K 9/107* | (2006.01) |

(52) U.S. Cl.
CPC .......... *A61K 9/1273* (2013.01); *A61K 9/1075* (2013.01); *A61K 31/4706* (2013.01); *A61K 31/52* (2013.01); *A61K 31/573* (2013.01); *A61P 37/06* (2018.01)

(58) Field of Classification Search
None
See application file for complete search history.

(56) References Cited

U.S. PATENT DOCUMENTS

2010/0222407 A1* 9/2010 Segura ................... A61P 43/00
514/44 A
2018/0022878 A1 1/2018 Scott et al.

OTHER PUBLICATIONS

Bobbala, S. et al. Flash nanoprecipitation permits versatile assembly and leading of polymeric bicontinuous cubic nanospheres+, *Nanoscale* 2018, 10(11):5078-5088.
Davidson, L.M. New Treatments for Systemic Lupus Erythematosus on the Horizon: Targeting Plasmacytoid Dendritic Cells to Inhibit Cytokine Production, *J. Clin. Cell Immunol* 2017, 8(6):534.
Karabin, N.B. et al. Sustained micellar delivery via inducible transitions in nanostructure morphology, *Nature Communications* 2018, 9:624.
Salama, A.D. et al. Challenges to achieving clinical transplantation tolerance, *J. Clin. Invest.* 2001, 108:943-948.
Salomon, B. et al. Complexities of CD28/B7: CTLA-4 costimulatory pathways in autoimmunity and translanation, *Ann. Rev. Immunol.* 2001, 19:225-252.
Shia, Yi. et al. Tailoring Nanostructure Morphology for Enhanced Targeting of Dendritic Cells in Atherosclerosis, *ACS Nano.* 2016, 10(12): 11290-11303.
Yi, S. et al. Engineering Nanomaterial Morphology for Targeting Immune Cells in Atherosclerotic Mice, Chemistry of Life Processes Institute, Northwestern University 2016.

* cited by examiner

*Primary Examiner* — Alton N Pryor
(74) *Attorney, Agent, or Firm* — Marianne Fuierer; Tristan A. Fuierer; Casimir Jones, S.C.

(57) ABSTRACT

The present invention provides for delivery of therapeutic drug in a polymeric delivery system comprising a PEG-bl-PPS di-block polymer formed in a micelle, filomicelle, or polymersome structure, wherein the structure effectively binds and/or interacts through shape-based targeting with a targeted cell type.

18 Claims, 11 Drawing Sheets

SELF-ASSEMBLED PARTICLES FOR TARGETED DELIVERY OF IMMUNOMODULATORS TO TREAT AUTOIMMUNITY AND CANCER

CROSS-REFERENCE TO RELATED APPLICATION

This application claims priority to U.S. Provisional Patent Application No. 62/730,157 filed on Sep. 12, 2018, the contents of which are hereby incorporated by reference herein for all purposes.

BACKGROUND OF THE INVENTION

Technical Field

The present invention demonstrates the use of self-assembled di-block copolymer particles to deliver immunomodulatory drugs to specifically target tumor or immune cells. Different self-assembled shapes exhibit differential uptake by tumor cells and immune cell subsets showing enhanced efficacy of immunomodulators to suppress innate immunity in subject suffering from autoimmune disease and active innate immunity in subjects with cancer.

Related Art

Systemic lupus erythematosus (SLE) is a chronic progressive autoimmune disease characterized by pleiotropic organ/tissue involvement and clinical manifestations. The progression of the disease is punctuated by flares, which by definition require therapy modification. Uncontrolled SLE will lead to end organ damage with increased morbidity and mortality. The clinical manifestations are variegated and often in a single patient many organs and tissue are involved. Most commonly targeted tissues are skin (with the typical malar or butterfly rash), joints, and kidney, but practically any organ and tissue can be targeted.

Autoantibodies, such as anti-double-stranded deoxyribonucleic acid (anti-dsDNA) or anti-nuclear antibody (ANA), and have helped to define the autoimmune nature of SLE. These autoantibodies, however, are not pathognomonic. SLE, with its pleiotropic clinical manifestations and lack of specific autoantibodies is the archetype of the non-organ-specific autoimmune diseases. American College of Rheumatology (ACR) has developed an eleven-factor set of guidelines to diagnose SLE. This intrinsic complexity of diagnosis and monitoring disease progression has hampered the validation of new treatments.

The full pathogenic cascade leading to SLE, with all its clinical facets, is complex and not yet fully defined. Despite this, it is now well accepted that T cells have a pivotal role in SLE. SLE is characterized by hyper-responsive T cells, excessive autoantibody production, and antigen presenting cell (APC) hyperactivation. The autoantibodies (in particular, anti-nuclear antibodies, and anti-dsDNA antibodies) in SLE patients are dependent on T-cell help that is provided by co-stimulatory molecules and cytokines. In addition to providing B-cell help, T cells can directly infiltrate the joints, skin, kidney, and brain, causing damage directly through cytotoxicity or indirectly through the recruitment and activation of macrophages and neutrophils.

Lymphocytes from patients with SLE show signs of increased activation; e.g., the percentage of $CD4^+$ T cells expressing CD25 increases as does the expression of CD86 on $CD19^+$ B cells. The increased CD86 expression is thought to render (autoreactive) B cells more susceptible to T-cell help and thus facilitate autoantibody production. Consistent with this observation, the number of activated B cells and levels of anti-dsDNA antibodies increase with disease activity. In addition, peripheral blood dendritic cells (DCs) and DCs derived from peripheral blood monocytes of SLE patients show increased expression of CD86 and the ratio of CD86/CD80 is higher in SLE patients compared with healthy donors. Unlike CD86, CD28 expression on $CD4^+$ and $CD8^+$ T cells in lupus patients appears to be more variable. Regardless of the levels of CD28 expression, T cells from SLE patients appear to be more responsive to anti-CD28-mediated activation and patients with active disease have increased gene expression of CD28 when compared to normal controls. CTLA4 (a co-inhibitory molecule) is also increased in T cells from SLE patients but this does not seem to control aberrant T-cell activation. Taken together, these data suggest that the CD28-CD86/CD80 pathway plays a central role in the defective immune response observed in SLE patients.

Currently, SLE patients are treated, depending on the severity of the disease, with antimalarials, corticosteroids (such as oral methylpredinisone), and immunosuppressive drugs such as methotrexate (MTX), azathioprine (AZA), mycophenolate mofetil, and cyclophosphamide. Although corticosteroids and immunosuppressive drugs are generally effective in temporarily controlling flares and disease progression, their limited efficacy and serious adverse effects significantly limit their prolonged use. This has led to the off-label use of many medicines to treat lupus patients. The paucity of satisfactory therapeutic options is highlighted by the approval of only one new medicine (Belimumab) for SLE in the last fifty years. Despite Belimumab approval SLE patients still have a very high unmet medical need and novel therapies are needed to satisfactorily treat SLE.

Inhibition of CD28-mediated T cell activation could inhibit undesired T cell responses occurring during autoimmunity, transplant rejection, or allergic responses. For example, inhibiting CD28 mediated T cell activation could delay graft rejection, prevent acute allograft rejection, induce donor specific tolerance, and prevent development and interrupt the progression of chronic allograft rejection, as well as prevent graft versus host disease (GVH), i.e., when transplanted T cells mount a vigorous immune response against host tissue alloantigens (1). Not only would inhibiting CD28-mediated T cell activation dampen the immune response through negating activation signaling through CD28, it should not impact the interaction of CD86 and CD80 to CTLA4, thereby preserving CTLA4-mediated inhibition of the T cell response. Thus, inhibiting CD28 mediated T cell activation could be used to prevent induction of autoimmunity and moderate the progression and/or severity of lupus as well as other autoimmune diseases (2).

Accordingly, it is an object of the present invention to provide improved methods for treating subjects with SLE, other autoimmune diseases, and cancer to overcome the shortcomings of the prior art.

SUMMARY OF THE INVENTION

The present invention provides for delivery of therapeutic drug in a polymeric delivery system comprising a PEG-bl-PPS di-block polymer formed in a micelle, filomicelle, polymersome or other type structures formed by the PEG-bl-PPS di-block polymers, wherein the structure effectively binds and/or interacts through shape-based targeting with a targeted cell type.

The present invention is effective wherein the disease or disorder is systemic lupus erythematosus, lupus nephritis, minimal change disease, focal segmental glomerulosclerosis, IgA nephropathy, transplant rejection, rheumatoid arthritis, osteoarthritis, psoriasis, ankylosing spondylitis, vasculitis, multiple sclerosis, systemic sclerosis, gout, uveitis, asthma, cystic fibrosis, chronic obstructive pulmonary disease, atopic dermatitis (eczema), sepsis, inflammatory bowel disease, trauma brain injury, spinal cord injury, ischemia reperfusion injury, heterotopic ossification, or granuloma, etc.

The delivery system can be formulated in an oral, nasal, ophthalmic drop, topical, buccal, sublingual, rectal, vaginal, intravenous, or other parenteral form, such as implants.

In one aspect, the present invention provides for a composition comprising a therapeutically effective amount of chloroquine or hydroxychloroquine to treat systemic lupus erythematosus, wherein the chloroquine is encapsulated and/or adsorbed on a polymeric delivery system, wherein the polymeric delivery system comprises a PEG-bl-PPS di-block polymer formed in a micelle, filomicelle, or polymersome structure, wherein the structure effectively binds and/or interacts through shape-based targeting of immune cell types. Importantly, the shape-based targeting increases the efficacy of the dose and accelerates the activity of the chloroquine.

Preferably the immune cell types include but are not limited to B cells or pDCs to reduce an autoimmune response.

In yet another aspect, the present invention provides for a method of treating a disease or disorder associated with lupus, the method comprising administering to a subject a therapeutic amount of chloroquine to treat the disease or disorder associated with lupus, wherein the chloroquine is encapsulated and/or adsorbed on a polymeric delivery system, wherein the polymeric delivery system comprises a PEG-bl-PPS di-block polymer formed in a micelle, filomicelle, or polymersome structure, wherein the structure effectively binds and/or interacts through shape-based targeting of immune cell types.

Figure 2:
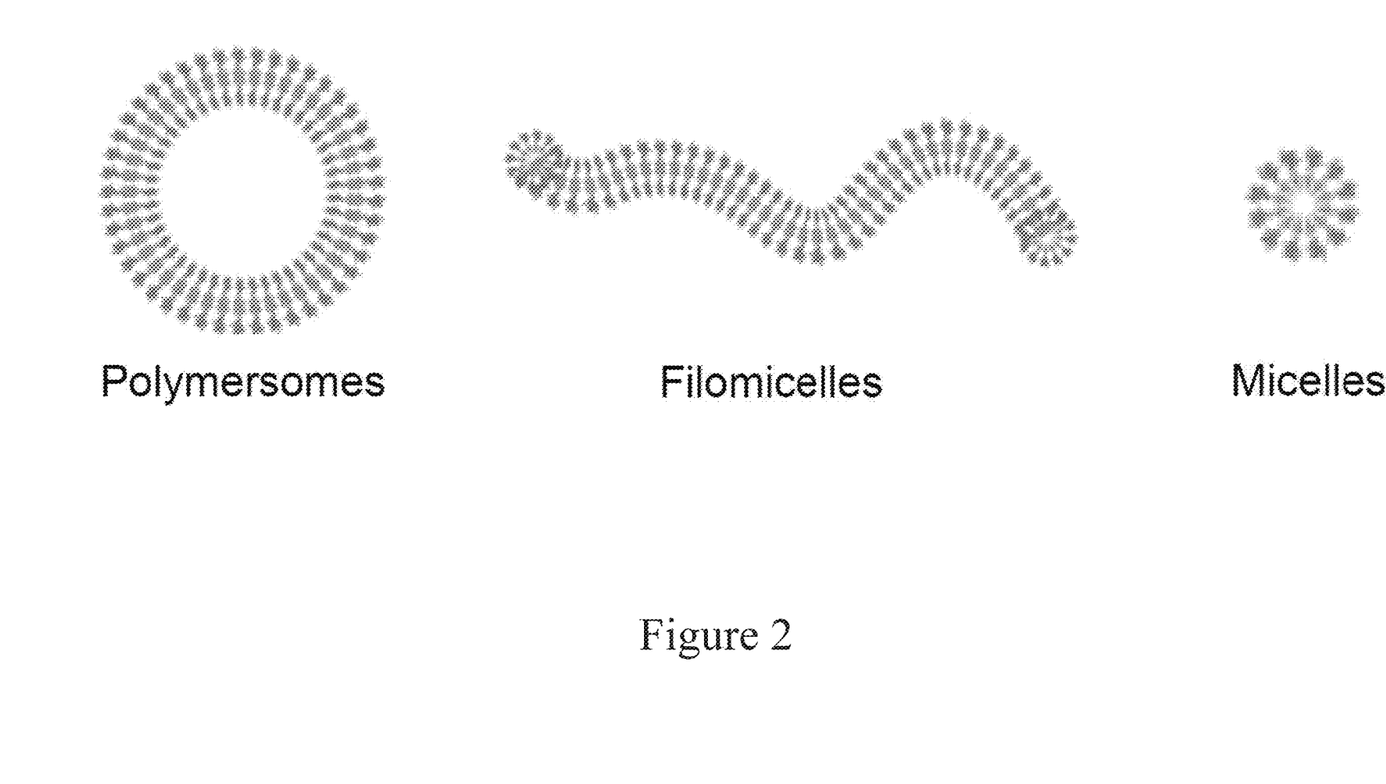
FIG. 2 shows the differences in the PEG-bl-PPS morphology determines the structure of shape including polymersomes, filomicelles, and micelles and retention of drug payload and uptake by specific immune cells.

The synthesized, self-assembled PEG-bl-PPS di-block copolymers can include different degrees of polymerization, for example, a $PEG_n$ block wherein "n" ranges from about 1:5 to about 50, and wherein the "n" of the $PPS_n$ block can range from about 15 to about 50. For example, a block copolymer can form a micelle (MC) with a structure of about $PEG_{45}$-bl-$PPS_{20}$; a structure of about $PEG_{17}$-bl-$PPS_{30}$ will form a polymersome (PS) and a structure of about $PEG_{44}$-bl-$PPS_{45}$ will form a filomicelle (FM) as shown in FIG. 2.

In a further aspect, the present invention provides for a composition comprising a therapeutically effective amount of a cancer treating drug to treat cancer, wherein the cancer treating drug is encapsulated and/or adsorbed on a polymeric delivery system, wherein the polymeric delivery system comprises a PEG-bl-PPS di-block polymer formed in a micelle, filomicelle, or polymersome structure, wherein the structure effectively binds and/or interacts through shape-based targeting with a targeted tumor cell.

Notably, the subject treated is a mammalian animal, such as human, dog, cat, horse, and so on. In one embodiment, the subject is a human.

Other aspects and features of the invention will be more fully apparent from the ensuing disclosure and appended claims.

BRIEF DESCRIPTION OF THE FIGURES

FIGS. 1A and B; FIG. 1A shows a schematic of chloroquine loaded PEG-bl-PPS filomicelles (FMs) in SLE. Chloroquine loaded FMs target pDCs, prevent TLR7 and TLR9 activation and mitigate proinflammatory responses via type I interferon cytokine production, plasma cell differentiation, and immune complex formation (3). FIG. 1B shows a schematic of PEG-bl-PPS polymer shapes targeting tumor cells and immune cells for cancer immunotherapies.

FIGS. 3A and B shows FEI Morgagni M268 100 kV transmission electron microscopy (TEM) images of chloroquine.

FIGS. 4A and 4B.

FIGS. 5A and 5B shows (1,1'-dioctadecyl-3,3,3',3'-tetramethylindotricarbocyanine perchlorate) DiD loaded nanoparticles cultured with frozen hPBMCs for 8, 24 and 48 hours in RPMI 1640 with 10% FBS and 20 ng/mL IL-3 at 37° C. and 5% $CO_2$ (n=3). Error bar represents standard deviation. Graphs are normalized to hPBMCs without nanoparticles.

FIGS. 7A &B.

DETAILED DESCRIPTION OF THE INVENTION

Figure 1:
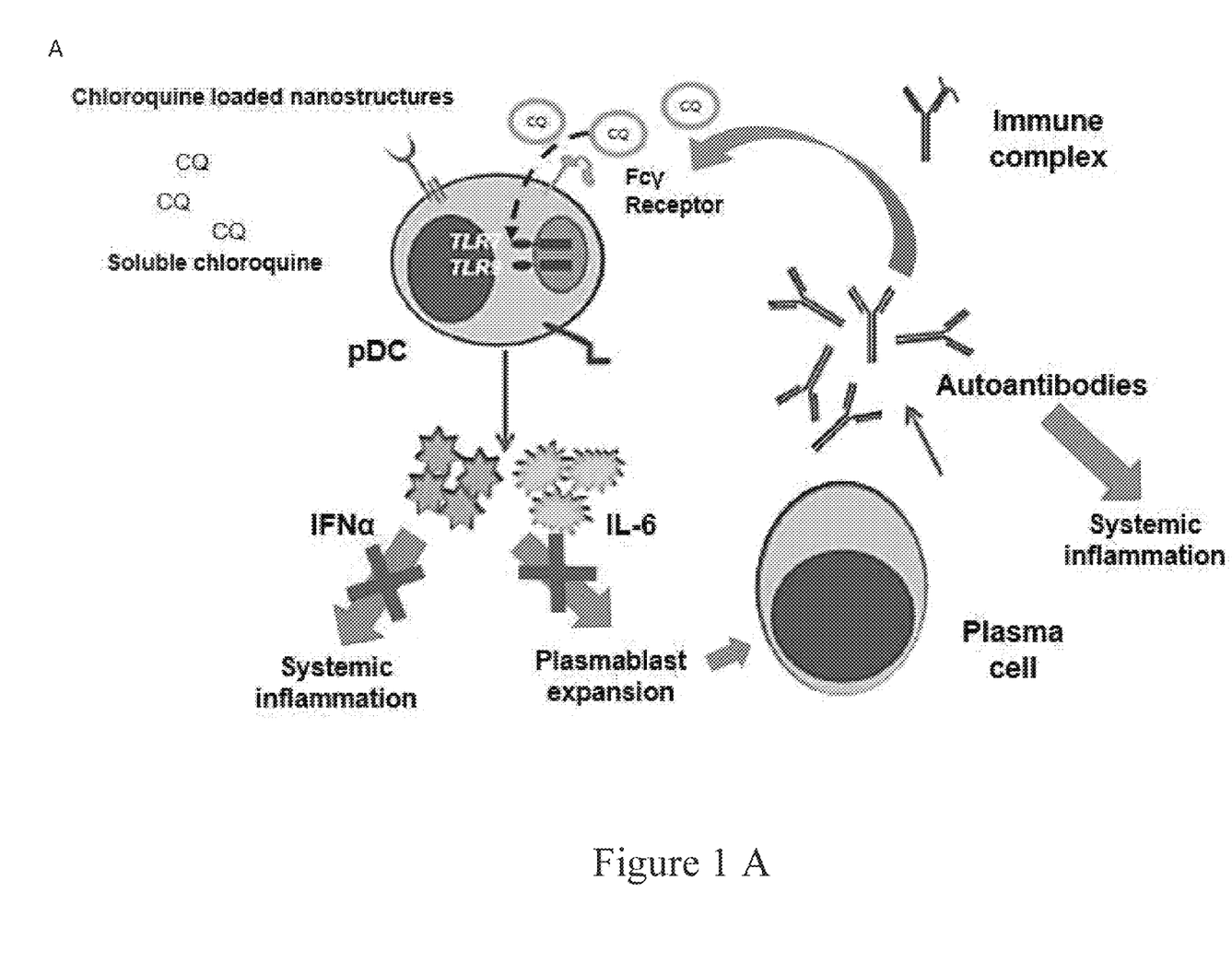

Systemic lupus erythematosus (SLE) is an autoimmune disease where the body attacks its healthy tissue and organs via autoantibody and nuclear antigen immune complexes. These complexes activate plasmacytoid dendritic cells (pDCs) and B cells via toll-like receptors (TLRs)-7 and -9 leading to inflammatory type I interferon cytokine production, triggering further autoantibody production by self-reactive B cells and worsening disease severity as shown in FIG. 1. As described herein, the present invention inhibits such activation. Antimalarials, such as chloroquine (CQ), are FDA-approved treatments for SLE and have been prescribed for SLE patients since the 1950s due to their low cost, limited, mild side effects and safety for pregnant women. Antimarlarials work by causing conformational changes to nucleic acid immune complexes, masking the TLR-binding epitope and preventing the production of inflammatory cytokines such as interferon-alpha (IFNα).

A major limitation of antimalarials is their delayed therapeutic efficacy, requiring up to 6 months of continuous treatment before the patient receives any benefits from the drug. Notably, CQ treatment requires months before achieving therapeutic efficacy. The present invention uses self-assembled di-block copolymer nanoparticles, poly(ethylene glycol)-bl-poly(propylene sulfide) (PEG-bl-PPS), to deliver CQ to pDCs and B cells via passive, shape-based targeting. CQ loaded PEG-bl-PPS nanoparticles of varying shapes can directly target immune cell types, such as pDCs and B cells, increasing the efficacy per dose and accelerating the activity of CQ versus systemic administration of the drug. The results of the present invention show that filamentous micelle polymers (FMs) loaded with CQ accelerates drug activity by directly delivering CQ to immune cells via passive, shape-based targeting.

Notably, depending on the individual block lengths, these copolymers can be engineered to assemble into a variety of different nanostructures in aqueous solutions, including spherical micelles, vesicles (i.e., polymersomes), and filamentous wormlike micelles (i.e., filomicelles). The filomicelles of the present invention are prepared by the assembly of PEG and hydrophobic PPS blocks. Such PEG-bl-PPS, a diblock copolymer poly(ethylene glycol)-block-poly(propylene sulfide) and production of same is described in U.S. Patent Publication No. 2018/002287, the content of which are incorporated by reference herein for all purposes. According to the specification in this cited U.S. patent publication, the copolymers are PEG-bl-PPS assembled by a flash nanoprecipitation method that encapsulate hydrophobic molecules, hydrophilic molecules, bioactive protein therapeutics, or other target molecules in amphiphilic copolymer nanocarriers.

The method of assembly of the FM include the following steps as described in the cited publication and briefly includes the steps of a flash precipitation method comprising;

(i) providing an organic phase solution comprising an amphiphilic copolymer and a process solvent, wherein the amphiphilic copolymer is poly(ethylene glycol)-bl-poly (propylene sulfide) (PEG-bl-PPS) and has a glass transition temperature below 0° C. and preferably from −40° to −0°;

(ii) providing an aqueous phase solution comprising an aqueous solvent, such as water;

(iii) mixing by multiple impingement, the organic phase solution, contain the chloroquine molecule and the aqueous phase solution to form a mixture; and (iv) introducing the mixture into a reservoir to cause precipitation of the amphiphilic copolymer as a nanocarrier of the chloroquine. Importantly, the organic solution and block copolymer are impinged upon an aqueous solution under turbulent wherein a supersaturated solution is generated by the turbulent mixing and such supersaturation induces precipitation of the block copolymer for stabilization of monodisperse nanoparticles which are loaded the target molecule chloroquine.

The synthesized, self-assembled PEG-bl-PPS di-block copolymers can include different degrees of polymerization, for example, a PEGS block wherein "n" ranges from about 15 to about 50, and wherein the "n" of the $PPS_n$ block can range from about 15 to about 50. For example, a block copolymer can form a micelle (MC) with a structure of about $PEG_{45}$-bl-$PPS_{20}$; a structure of about $PEG_{17}$-bl-$PPS_{30}$ will form a polymersome (PS) and a structure of about $PEG_{44}$-bl-$PPS_{45}$ will form a filomicelle (FM) as shown in FIG. 2.

As discussed herein, the PEG-bl-PPS drug compounds disclosed herein can be administered in such oral dosage forms as tablets, capsules (each of which includes sustained release or timed release formulations), pills, powders (e.g., reconstitutable lyophilized powder), micronized compositions, granules, elixirs, tinctures, suspensions, ointments, vapors, liposomal particles, nanoparticles, syrups and emulsions. Likewise, they may also be administered in intravenous (bolus or infusion), intraperitoneal, topical (e.g., dermal, epidermal, transdermal, ophthalmically such as ocular eyedrop), intranasally, subcutaneous, inhalation, intramuscular or transdermal (e.g., patch, microneedles) form, all using forms well known to those of ordinary skill in the pharmaceutical arts. Again, the ordinarily skilled physician, veterinarian or clinician or a clinical pharmacist may readily determine and prescribe the effective amount of the drug required to prevent, counter or arrest the progress of the condition.

The compounds of the present invention may be used in combination with other drugs or therapies having similar or complementary effects to those of the compounds disclosed herein. The individual components of such combinations can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly.

As used herein, the term "composition," "pharmaceutical composition," or the like, is intended to encompass a product comprising the specified ingredients in the specified amounts, as well as any product which results, directly or indirectly, from combination of the specified ingredients in the specified amounts.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Experimentation

Systemic lupus erythematosus (SLE) is an autoimmune disease that attacks healthy organs via circulating immune complexes. Complexes activate immune cells via toll-like receptors (TLRs) 7 and 9, driving inflammatory type I interferon secretion. Chloroquine (CQ) is an FDA-approved TLR antagonist that mitigates inflammation in SLE, but CQ treatment requires months before achieving therapeutic efficacy. The present invention overcomes such a delay by a polymeric delivery system.

Nanoparticles (NPs) are materials with dimensions between 1 and 100 nanometers that have applications in medicine, consumer products and optics. Self-assembled NPs derived from poly(ethylene glycol)-bl-poly(propylene sulfide) (PEG-bl-PPS, as discussed above, form different geometries based on their ratio of hydrophilic PEG to hydrophobic PPS. The differences in structure influences shape, retention of drug payload and uptake by specific immune cells. The present invention shows that filamentous micelle polymers (FMs) ($PEG_{44}$-bl-$PPS_{45}$) loaded with CQ accelerates drug activity by directly delivering CQ to immune cells via passive, shape-based targeting. Further, human blood immune cells were pretreated with soluble CQ or CQ in FMs, the cells were stimulated with a TLR9 agonist, and type I interferon response was analyzed via MX1 gene expression using real-time RT-PCR. The results shown herein indicate that CQ-FMs decreased MX1 gene expression similar to soluble CQ, while CQ in control polymer PLGA spheres had no effect. These results show FMs can increase CQ efficacy per dose for SLE-relevant pathways.

Filomicelle PEG-bl-PPS nanoparticles (FMs) obtained from Northwestern University were assembled via thin film hydration. PLGA NPs were assembled via double-emulsion and served as a NP control. Chloroquine (CQ) was loaded in PEG-bl-PPS. Chloroquine diphosphate was loaded in PLGA. Different CQ drugs were used based on loading methods and polymer properties. CQ loaded and unloaded FMs were stained with 2% uranyl acetate and imaged using the FEI Morgagni M268 100 kV transmission electron microscopy (TEM). Loaded FMs were hydrolyzed in dimethyl sulfoxide (DMSO) and measured using Mettler Toledo UV5 Nano. Human peripheral blood mononuclear cells (PBMCs) were isolated from buffy coats using Ficoll-Paque medium density gradient. To check for FM cell distribution and plasmacytoid dendritic cell (pDC), myeloid dendritic cell (mDC) and B cell frequencies in PBMCs, cells were incubated with DiD loaded FMs for 8, 24 and 48 hours in RPMI 1640 with 10% FBS and 20 ng/mL IL-3 and stained with fluorescent antibodies for the following markers: CD123 (PE), CD1c (APC/Cy7), CD19 (BV 421) and Zombie Aqua. Flow cytometry samples were acquired on a CyAn™ ADP High-Performance Flow Cytometer instrument using Summit Software. Data analysis was performed using FlowJo v10 10.1r7. Cell populations were determined using frequency of total events and cell distribution from median fluorescent intensity. Cells were treated for 1 hour with soluble drug or drug loaded nanoparticles. Cells were then stimulated with CpG Class A for 6 hours. Reverse transcription polymerase chain reaction (RT-PCR) was used to analyze downstream IFN-response gene MX1. Expression levels were normalized to β-actin control.

Figure 3A:
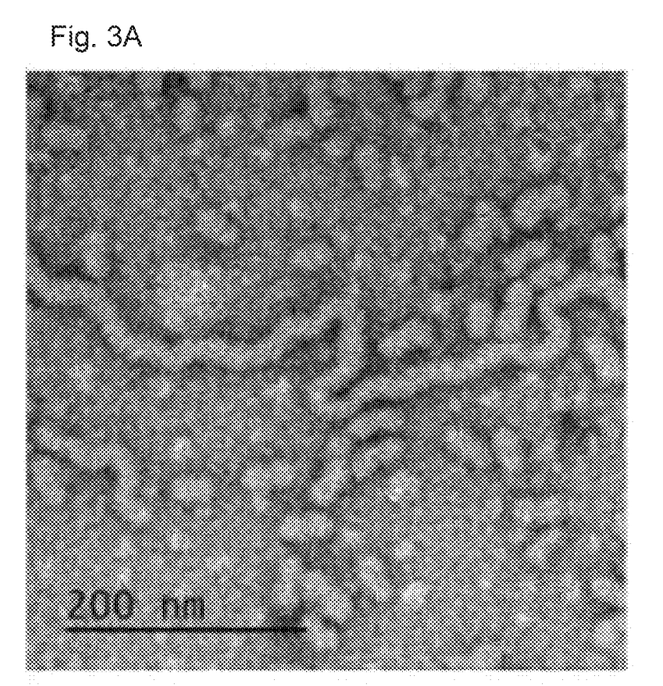
FIG. 3A shows loaded and FIG. 3B shows unloaded filomicelle PEG-bl-PPS at 12 mg/mL. Samples were stained with 2% uranyl acetate.
Figure 3B:
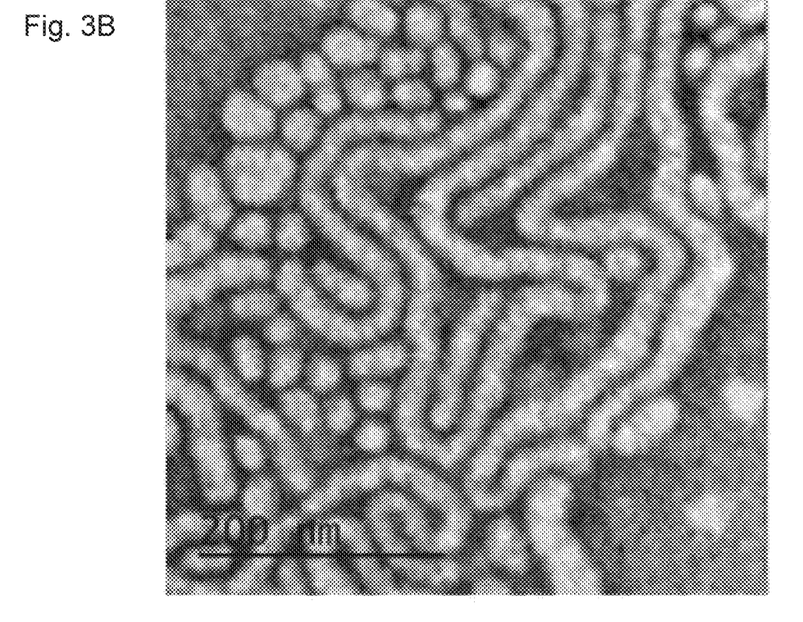
Figure 4A:
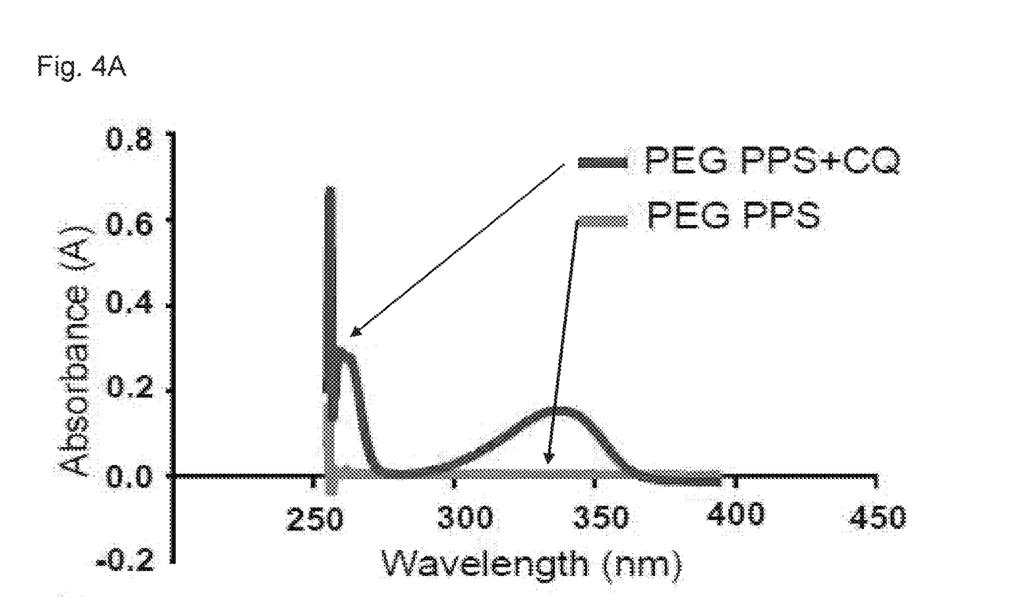
FIG. 4A shows the absorbance of unloaded and chloroquine loaded PEG-bl-PPS filomicelles at chloroquine excitation wavelength of 334 nm using UV-Vis. Normalized to baseline (PEG PPS).
Figure 4B:
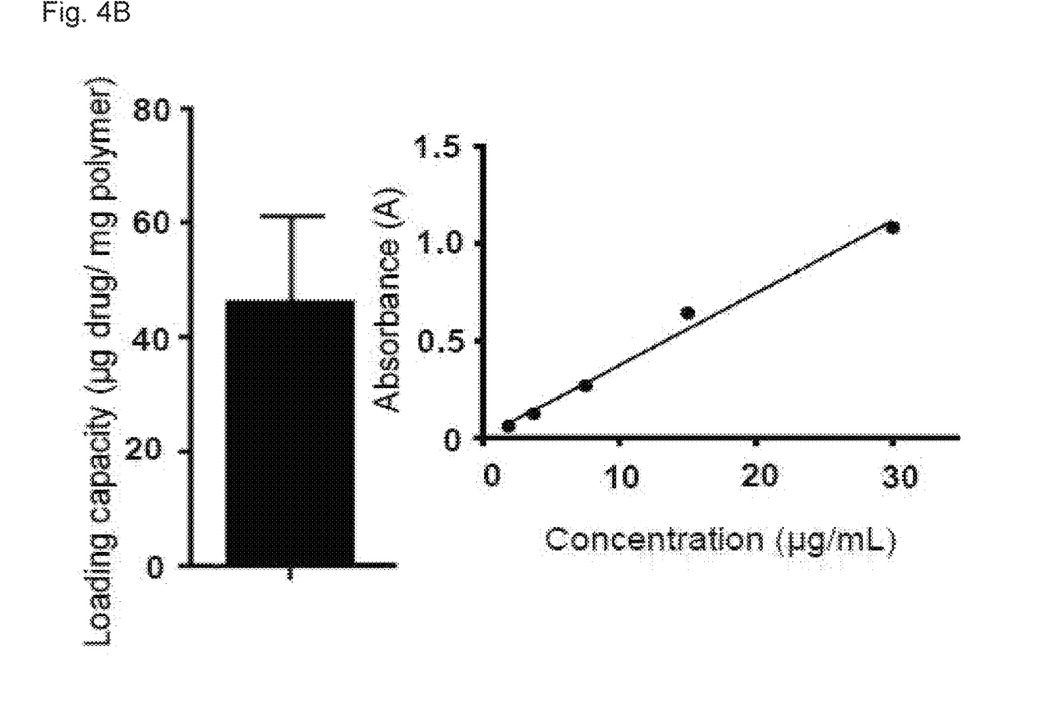
FIG. 4B shows the average loading capacity of chloroquine loaded PEG-bl-PPS nanoparticles via thin-film hydration is 46.905±12.108 μg drug/mg polymer (n=3). Error bar represent standard deviation. Standard curve of chloroquine dissolved in DMSO used for loading capacity calculations. $Y=0.037X+0.005094$ where Y is absorbance and X is concentration. $R2=0.9879$.
Figure 10:
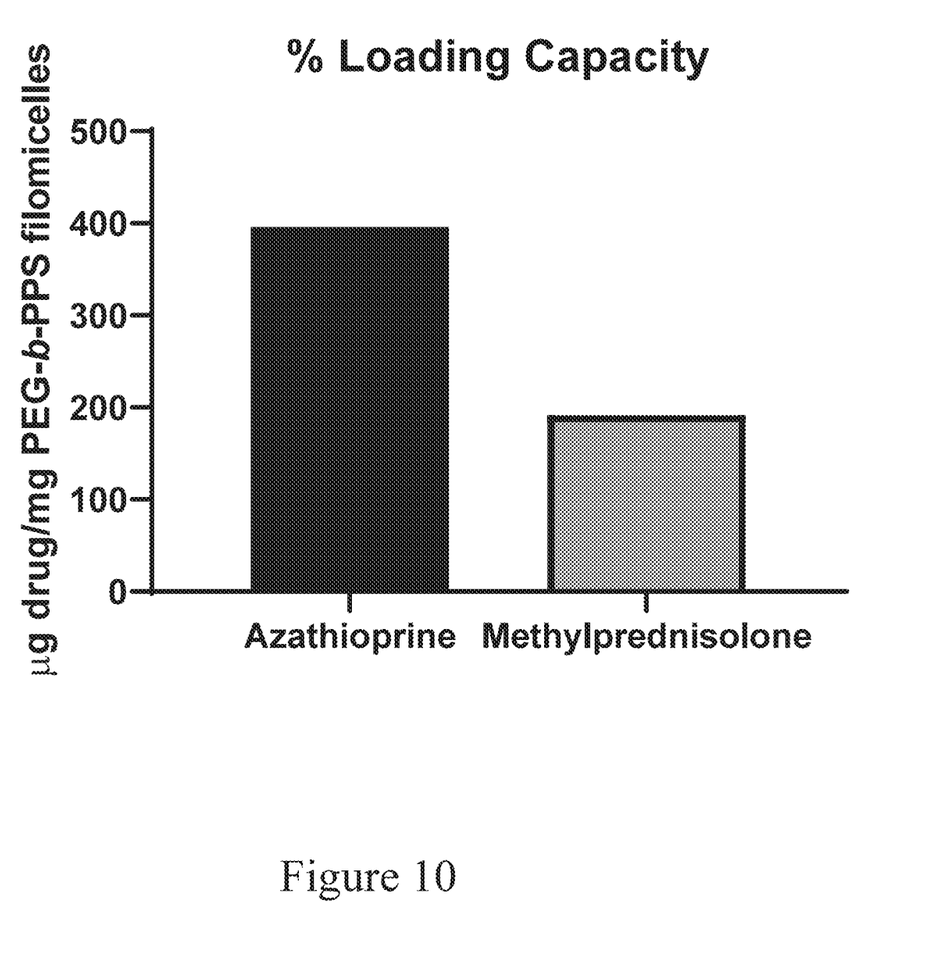
FIG. 10 shows the loading capacity of the filomicelles (PEG PPS) with other immunosuppressives used in lupus.

Characterization of CQ loaded FMs showed an average loading capacity of 46.905 μg drug/mg polymer and average encapsulation efficiency of 49.5%. Transmission electron microscopy (TEM) images of loaded and unloaded FMs show no difference in morphology or structure, as shown in FIG. 3. Notably, in FIG. 10, it is shown that other lupus treating drugs can also be loaded into the filomicelles (PEG-PPS) such as AZA load at almost 400 ug/mg of mg of filomicelles and methylprednisolone at about 200 ug drug to mg of filomicelles.

Figure 5A:
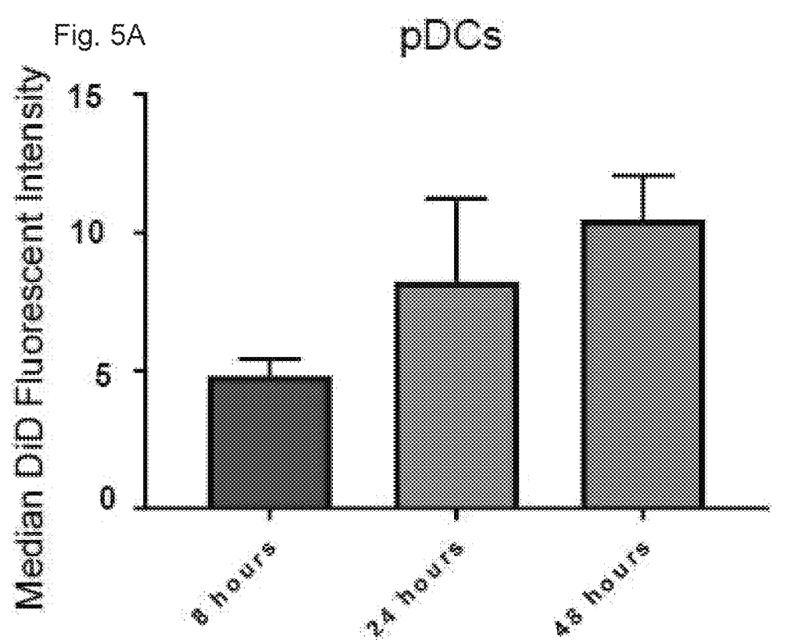
FIG. 5A shows plasmacytoid dendritic cells (pDCs) and FIG. 5B shows B cells were analyzed for nanoparticle distribution via flow cytometry.
Figure 5B:
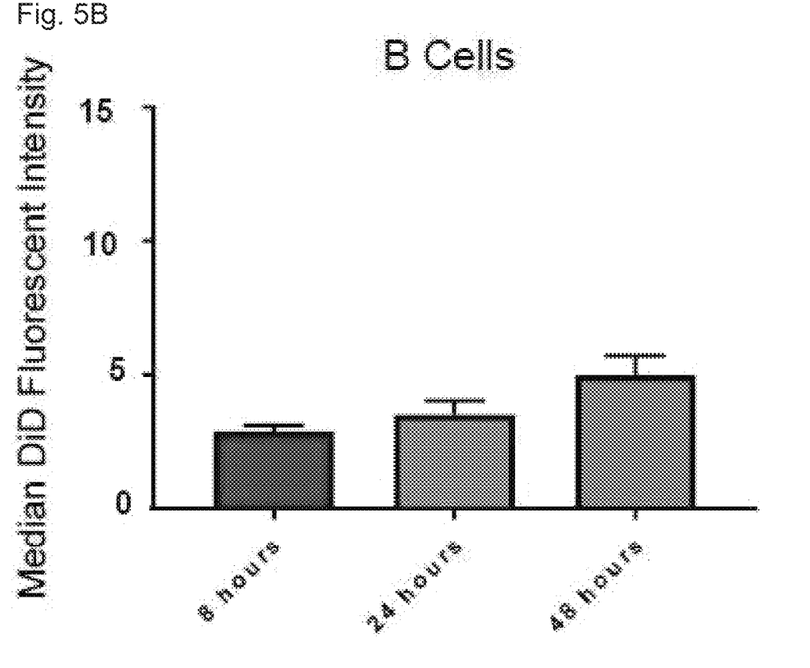

PEG-bl-PPS NPs target immune cells, pDCs and B cells, important in SLE pathogenesis and TLR-7 and -9 induced inflammatory responses. The differences in PEG-bl-PPS morphology, such as polymersomes, filomicelles, and micelles, is to deliver toll-like receptor (TLR)-7 and -9 antagonist drugs to immune cells, such as pDCs and B cells, important in SLE pathogenesis and severity. CQ-loaded FMs are an effective targeted drug delivery vehicle for suppressing TLR7 and activation in B cells and pDCs, the major pathways responsible for SLE pathogenesis and end-stage symptoms such as nephritis. FIG. 5 shows DiD loaded nanoparticles cultured with frozen hPBMCs for 8, 24 and 48 hours in RPMI 1640 with 10% FBS and 20 ng/mL IL-3 at 37° C. and 5% $CO_2$ (n=3). Both plasmacytoid dendritic cells (pDCs) and B cells were analyzed for nanoparticle distribution via flow cytometry. Clearly the FM were more effective in the B cells.

Figure 6:
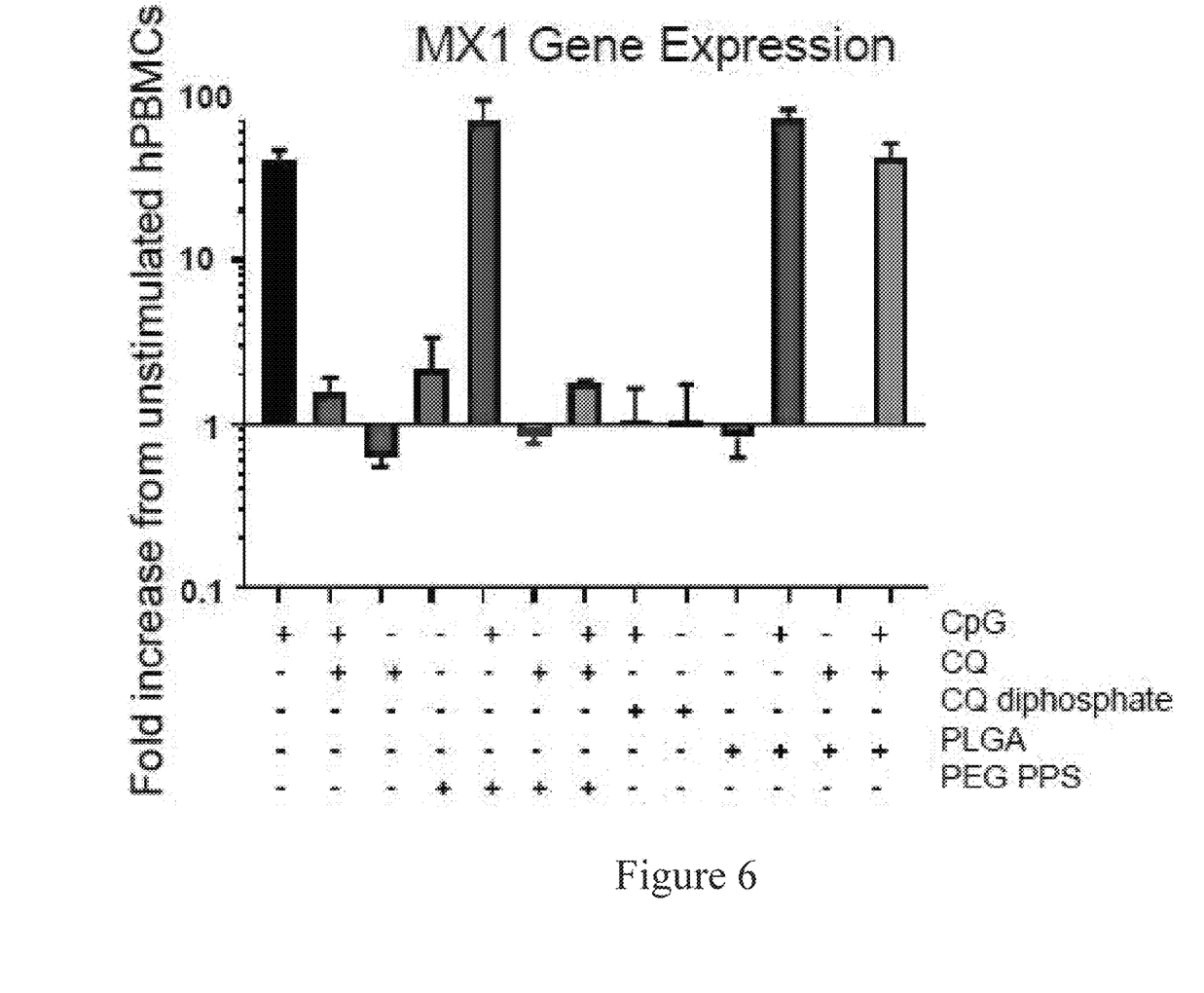
FIG. 6 shows the average MX1 gene expression (n=2) of fresh hPBMCs using real-time PCR (RT-PCR) after pre-incubation with soluble chloroquine or chloroquine loaded nanoparticle for 1 hour and stimulation with TLR9 agonist, CpG, for 6 hours. MX1 is upregulated in SLE patients versus healthy patients. Error bars show standard deviation.
Figure 9:
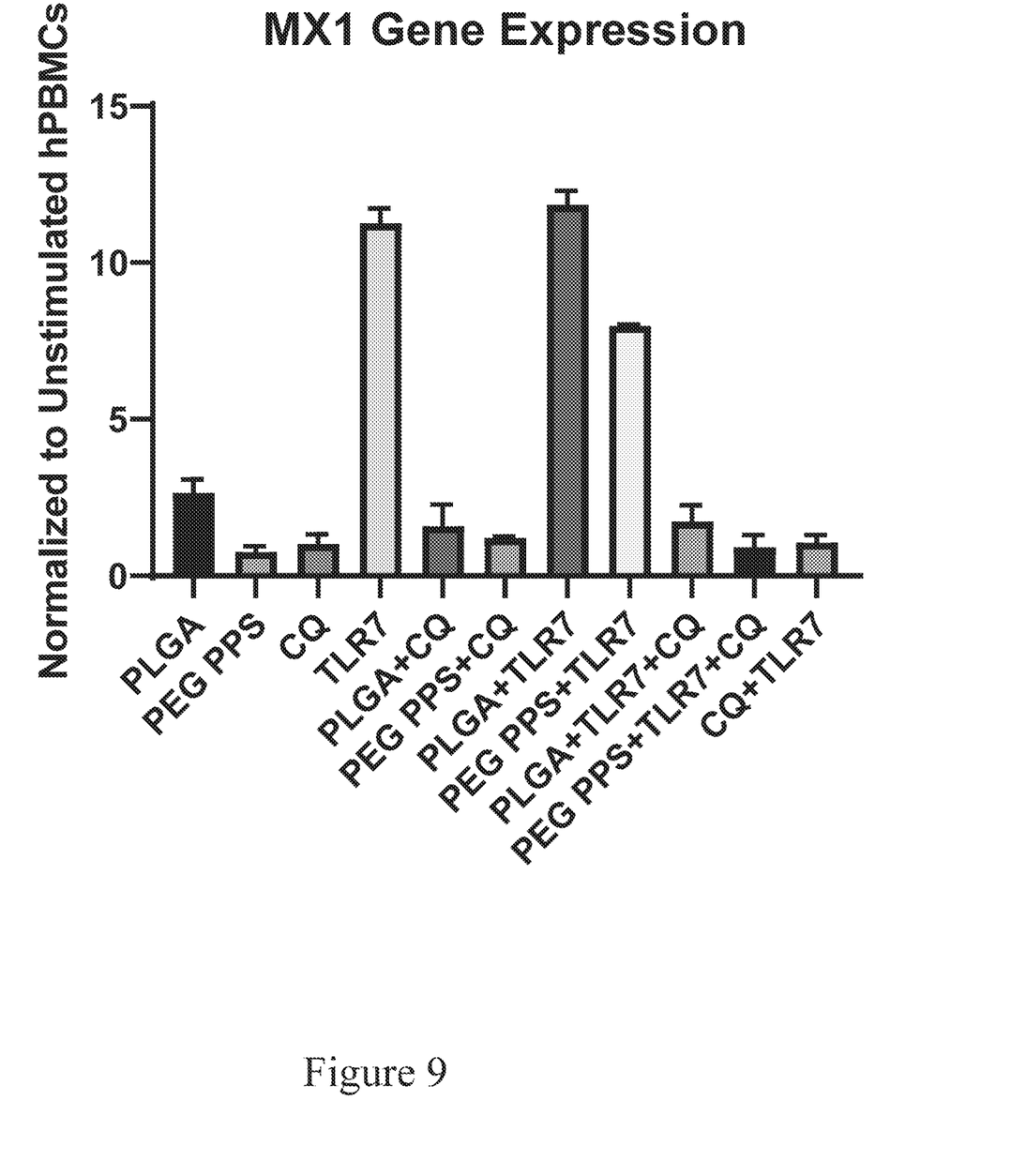
FIG. 9 shows results of filomicelle (PEG PPS)+CQ for inhibiting RNA stimulation of TLR7.

CQ loaded PEG-bl-PPS decreased MX1 expression similar to soluble condition. CQ loaded in PLGA had no effect on MX1 gene expression. It was found that CQ-loaded filamentous micelle PEG-bl-PPS nanoparticles (FMs) decreased MX1 gene expression in human peripheral blood mononuclear cells (hPBMCs) similar to soluble CQ. As shown in FIG. 6, CQ loaded in a polymer control, poly(lactic-co-glycolic acid) (PLGA) spheres, exhibited no effect on MX1 gene expression. MX1 is a type I interferon-stimulated gene whose activity is directly induced by IFNα, a critical driver of inflammatory damage in SLE. However, when human blood immune cells were pretreated with soluble CQ or CQ in FMs, stimulated cells with a TLR9 agonist, and analyzed type I interferon response via MX1 gene expression using real-time RT-PCR. The results shown in FIG. 6 illustrate that CQ-FMs decreased MX1 gene expression similar to soluble CQ, while CQ in control polymer PLGA spheres had no effect. These results show FMs can increase CQ efficacy per dose for SLE-relevant pathways. These results are also shown in FIG. 9 where the filomicelle (PEG PPS)+CQ is better at inhibiting single-stranded RNA stimulation of TLR7 compared to PLGA+CQ.

In addition to the efficacy in SLE, the nanoparticle platform of the present invention was used to specifically target tumor cells and immune cells, such as myeloid derived suppressor cells (MDSCs), B cells and macrophages, important in supporting tumor growth by suppressing anti-tumor immunity as shown in FIG. 1B, which is a schematic of PEG-bl-PPS polymer shapes targeting tumor cells and immune cells for cancer immunotherapies. By directly targeting these cells, drug toxicity and severe side effects associated with current systemic cancer immunotherapies is reduced and the nanoparticle shape was used to deliver targeted immunotherapies to specific immunosuppressive cell types. The enclosed data show that PEG-bl-PPS polymer shapes, FMs, micelles (MCs), bicontinuous nanostructures (BCNs) and polymersomes (PSs), have different uptake patterns in murine stage IV metastatic breast cancer cell line, 4T1. MCs and FMs were taken up more than PSs and BCNs. Nanoparticles injected intratumorally in 4-9 month old Balb/c female mice with established 4T1 tumors showed that PSs were taken up B cells and MDSCs; whereas, MCs and FMs were taken up by macrophages and MDSCs.

Figure 7A:
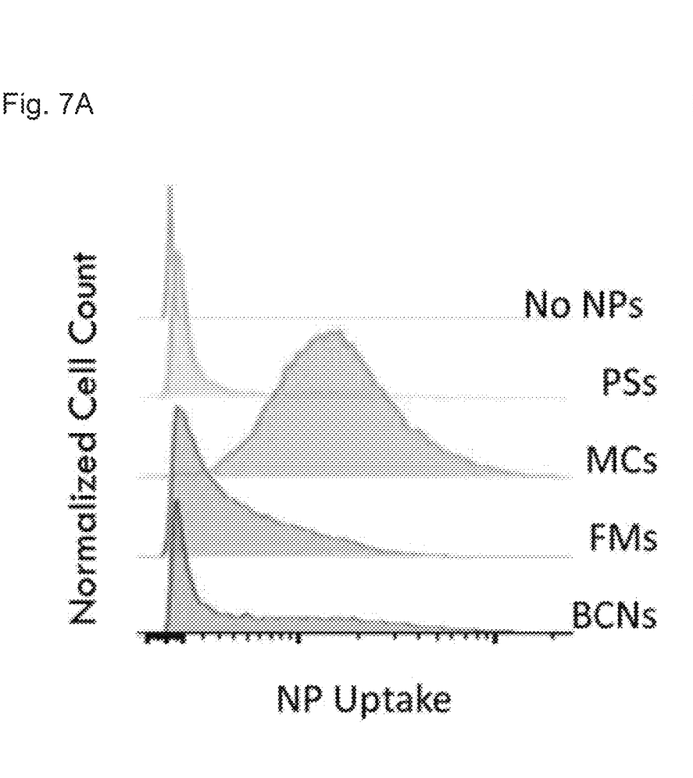
FIG. 7A shows the nanoparticle (NP) uptake of murine breast cancer 4T1 cells in vitro by flow cytometry after 24 hours (n=3).
Figure 7B:
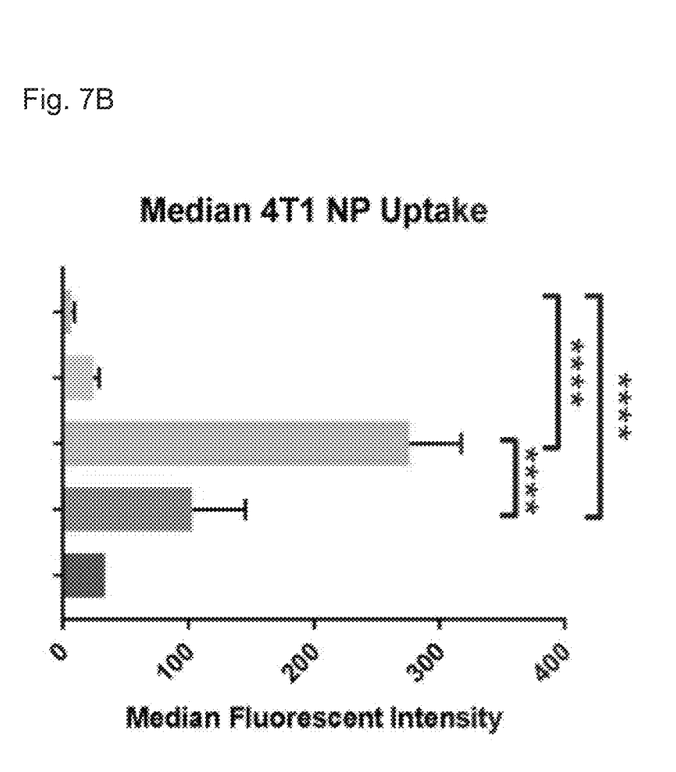
FIG. 7B shows the median fluorescent intensity of data is FIG. 7A. (FM=PEG 44 PPS 45, MC=PEG 45 PPS 20, PS=PEG 17 PPS 44)
Figure 8A:
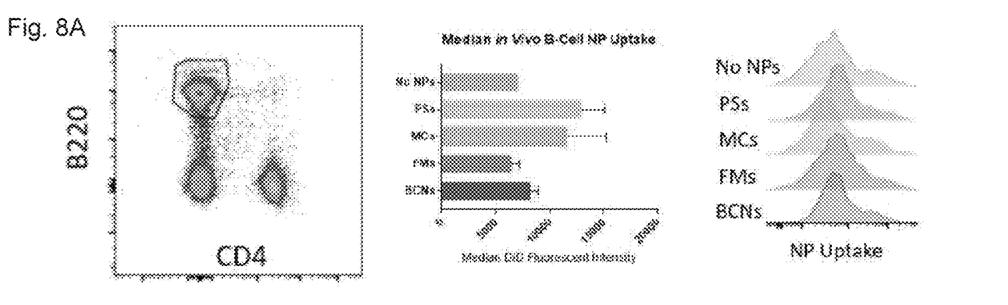
FIGS. 8A, 8B and 8C shows the DiD loaded nanoparticles injected intratumorally in 4-9 month old Balb/c female mice with 4T1 tumors (n=2). Error bar represents range. Tumors were removed, enzymatically dissociated and analyzed for nanoparticle distribution for FIG. 8A B cells, FIG. 8B macrophages and FIG. 8C myeloid derived suppressor cells (MDSCs) via flow cytometry.
Figure 8B:
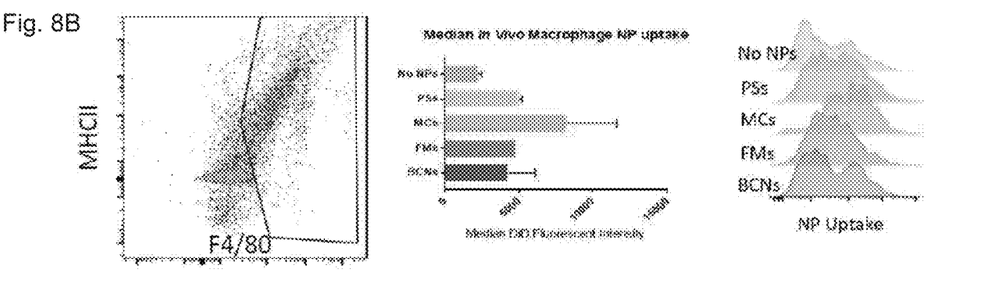
Figure 8C:
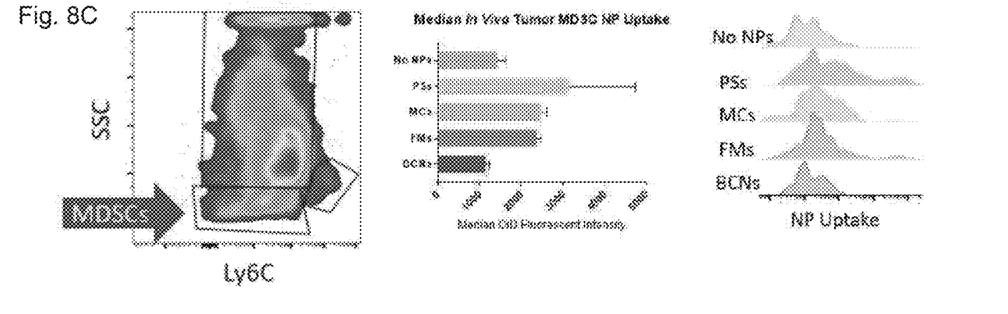

FIG. 7 shows the nanoparticle (NP) uptake of murine breast cancer 4T1 cells in vitro by flow cytometry after 24 hours (n=3). Notably, the MCs and FMs were taken by 4T1 significantly more than PSs and BCNs (two-way ANOVA p<0.0001) and uptake was significantly more in MCs compared to FMs (two-way ANOVA p<0.0001). The results in FIG. 8 shows DiD loaded nanoparticles injected intratumorally in 4-9 month old Balb/c female mice with 4T1 tumors (n=2). When the tumors were removed, enzymatically dissociated and analyzed for nanoparticle distribution for (A) B cells, (B) macrophages and (C) myeloid derived suppressor cells (MDSCs) via flow cytometry. As viewed in FIG. 8, different structures were more effective in the different types of cells, for example the polymersomes were more effective in delivery in B-cells, the micelles were more effective delivery in macrophages and again delivery by the polymersomes were the most effective delivery shape in the Tumor MDSC cancer cells.

In conclusion, the results shown herein show a multifunctional approach to 1) reduce drug toxicity of systemic administration of clinically accepted drugs, 2) utilize nanoparticle shape to target different immune cells based on disease model 3) improve efficacy per drug dose.

REFERENCES

The contents of all references cited herein are incorporated by reference herein for all purposes.
1. Salama et al. (2001) *J. Clin. Invest.* 108: 943-48).
2. Saloman et al. (2001) *Ann. Rev. Immunol.* 19: 225-252).
3. Davidson, L. M. and Jorgensen, T. N. (2017) *J Clin Cell Immunol;* 8(6): 534.
4. U.S. Patent Publication No. 2018/0022878
5. Sijia Yi, et al. (2016); Tailoring Nanostructure Morphology for Enhanced Targeting of Dendritic Cells in Atherosclerosis, *ACS Nano.* 10(12): 11290-11303.

That which is claimed is:

1. A composition comprising a therapeutically effective amount of chloroquine or hydroxychloroquine to treat systemic lupus erythematosus, wherein the chloroquine or hydroxychloroquine in the composition is encapsulated and/or adsorbed on a polymeric delivery system, wherein the polymeric delivery system comprises a PEG-bl-PPS di-block polymer formed in a micelle, filomicelle, or polymersome structure, wherein the structure effectively binds through shape-based targeting of immune cell types to reduce an autoimmune response, wherein the immune cell types comprise B cells or plasmacytoid dendritic cells (pDCs).

2. The composition according to claim 1, wherein the shape-based targeting is effective in increasing efficacy of, and accelerating activity of, the chloroquine or hydroxychloroquine.

3. The composition according to claim 1, wherein the PEG-bl-PPS di-block copolymer comprises different degrees of polymerization, wherein "n" of a $PEG_n$ block is from about 15 to about 50, and wherein "n" of a $PPS_n$ block is from about 5 to about 50.

4. The composition according to claim 1, wherein the PEG-bl-PPS di-block copolymer is $PEG_{45}$-bl-$PPS_{20}$, $PEG_{17}$-bl-$PPS_{30}$, or $PEG_{44}$-bl-$PPS_{45}$.

5. The composition according to claim 1, wherein loading capacity of the PEG-bl-PPS di-block copolymer is about 40% to about 60%.

6. The composition according to claim 1, wherein the PEG-bl-PPS di-block copolymer is effective in decreasing MX1 gene expression.

7. The composition according to claim 1, wherein the composition is formulated in an administration form selected from the group consisting of oral, nasal, ophthalmic, topical, buccal, sublingual, rectal, vaginal, intravenous, intraperitoneal, subcutaneous, inhalation, intramuscular, and transdermal.

8. The composition according to claim 1, wherein the micelle, filomicelle, or polymersome structures are nanoparticles.

9. The composition according to claim 1, comprising a therapeutically effective amount of chloroquine.

10. A method of treating systemic lupus erythematosus, the method comprising:
administering to a subject a composition comprising a therapeutic dose of chloroquine or hydroxychloroquine to treat systemic lupus erythematosus, wherein the chloroquine or hydroxychloroquine is encapsulated and/or adsorbed on a polymeric delivery system, wherein the polymeric delivery system comprises a PEG-bl-PPS di-block polymer formed in a micelle, filomicelle, or polymersome structure, wherein the structure effectively binds and/or interacts through shape-based targeting of immune cell types to reduce an autoimmune response, wherein the immune cell types comprise B cells or plasmacytoid dendritic cells (pDCs).

11. The method according to claim 10, wherein the shape-based targeting increases efficacy of, and accelerates activity of, the chloroquine or hydroxychloroquine.

12. The method according to claim 10, wherein the PEG-bl-PPS di-block copolymer comprises different degrees of polymerization, wherein "n" of a $PEG_n$ block is from about 15 to about 50, and wherein "n" of a $PPS_n$ block is from about 5 to about 50.

13. The method according to claim 12, wherein the PEG-bl-PPS di-block copolymer is $PEG_{45}$-bl-$PPS_{20}$; $PEG_{17}$-bl-$PPS_{30}$ or$PEG_{44}$-bl-$PPS_{45}$.

14. The method according to claim 10, wherein loading capacity of the PEG-bl-PPS di-block copolymer is about 40% to about 60%.

15. The method according to claim 10, wherein the PEG-bl-PPS di-block copolymer decreases MX1 gene expression.

16. The method according to claim 10, wherein the composition is formulated in an administration form selected from the group consisting of oral, nasal, ophthalmic drop, topical, buccal, sublingual, rectal, vaginal, intravenous, intraperitoneal, subcutaneous, inhalation, intramuscular, and transdermal.

17. The method according to claim 10, wherein the micelle, filomicelle, or polymersome structures are nanoparticles.

18. The method according to claim 10, wherein the composition comprises a therapeutically effective amount of chloroquine.

* * * * *